United States Patent [19]

Clack et al.

[11] Patent Number: 5,039,797

[45] Date of Patent: Aug. 13, 1991

[54] 2'-O-(4-BENZOYL)BENZOYL NUCLEOSIDE CYCLIC MONOPHOSPHATE

[75] Inventors: James W. Clack, Branford; Peter J. Stein, Guilford, both of Conn.

[73] Assignee: Yale University, New Haven, Conn.

[21] Appl. No.: 421,441

[22] Filed: Oct. 13, 1989

[51] Int. Cl.$^5$ .................. A61K 31/70; C07H 19/167; C07H 19/16

[52] U.S. Cl. ........................................ 536/49; 536/27; 536/28

[58] Field of Search .............. 536/27, 28, 29; 514/47, 514/48, 51, 52, 912

[56] References Cited

PUBLICATIONS

The Journal of Biological Chemistry, vol. 249, No. 11, 1974, pp. 3510–3518, Photoaffinity Labeling of Peptide Hormoine Binding Sites; Richard E. Galardy et al.
The Journal of Biological Chemistry, vol. 257, No. 6, 1982, pp. 2834–2841, Exploring the Adenine Nucleotide Binding Sites on Mitochondrial $F_1$-ATPase with a New Photoaffinity Probe, 3'-O-(4-Benzoyl)benzoyl Adenosine 5-Triphosphate; Noreen Williams et al.
The Journal of Biological Chemistry, vol. 261, No. 24 pp. 11374–11377; 1986 3-O-(Benzoyl)benzoylcytidine 5-Triphosphate A Substrate and Photoaffinity Label for CMP-N-Acetyloneuraminic Acid Synthetase; Claudia Abeijon et al.
Analytical Biochemistry, vol. 60, (1974), pp. 163–169; 1,N$^6$-Etheno-2-Azadenosine 3'5'-Monophosphate: A New Fluorescent Substrate for Cycle Nucleotide Phosphodiesterase; K. C. Tsou et al.
Science, vol. 177, pp. 279–280; (1972) Fluorescent Modification of Adenosine 3'5'-Monophosphate: Spectroscopic Properties and Activity in Enzyme Systems J. A. Secrist et al.
Biochemistry, vol. 14, No. 17 (1975), pp. 3852–3857; Photoaffinity Labeling of Adenosine 3'5'-Cyclic Monophosphate Binding Sites of Human Red Cell Membranes; Boyd E. Haley.
The Journal of Biological Chemistry, vol. 257, No. 22, pp. 13354–13358, 1982 New Fluorescent Analogs of cAMP and cGMP Available as Substrates for Cyclic Nucleotide Phosphodiesterase; Toshiaki Hiratsuka.
Methods in Enzymology, XLIV, Adenosine', 5'-Cyclic Monophosphate Binding Sites pp. 339–346, (1977).

*Primary Examiner*—Johnnie R. Brown
*Assistant Examiner*—Gary L. Kunz
*Attorney, Agent, or Firm*—Sprung Horn Kramer & Woods

[57] ABSTRACT

The invention is a 2'-O-(4-benzoyl)benzoyl nucleoside 3', 5'-cyclic monophosphate of formula (I)

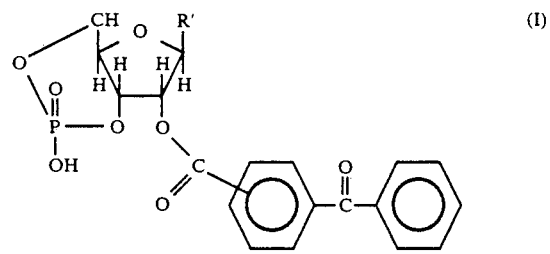

wherein R' is guanine or adenine. Also disclosed are topical pharmaceutical compositions and methods of using them for reducing intraocular pressure.

8 Claims, 8 Drawing Sheets

2'-O-(4-BENZOYL)BENZOYL NUCLEOSIDE CYCLIC MONOPHOSPHATE

BACKGROUND OF THE INVENTION

1. Field of the Invention

The present invention concerns 2'-0-(4-benzoyl)benzoyl nucleoside cyclic monophosphate and the use of the same as to reduce intraocular pressure 2. Background of the Invention The first report of benzoyl benzoyl derivatization was of the peptide hormone gastrin. This compound is unrelated to cyclic nucleotides and was employed as a photoaffinity probe for the gastrin receptor (R. E. Galardy, L. C. Craig, J. D. Jamieson and M. P. Printz, *J. Biol. Chem.*, 249, 3510, (1974)). Benzoyl benzoyl derivatives of adenosine 5'triphosphate (ATP) (N. Williams and P. S. Coleman, *J. Biol. Chem.*, 257, 2834–2841, (1982)), cytidine triphosphate (CTP) (C. Abeijon, J. M. Capasso, D. Tal, W. F. Vann and C. B. Hirschberg, *J. Biol. Chem.*, 261, 11374–11377, (1986)) and uridine 5'triphosphate (UTP) (C. Abeijon et al, supra) were subsequntly reported. In each of these nucleotide triphosphates, the benzoyl benzoyl moiety was added at the 3'position. Fluorobenzoyl adenosine 5'triphosphate has been synthesized, but the fluorobenzoyl moiety was added to the $N^6$ position on the base.

Derivatives of 3',5'cyclic guanosine monophosphate (cGMP) and 3',5'cyclic adenosine monophosphate (cAMP) which are useful as photoaffinity agents have been synthesized. Such derivatives differ from the inventive compounds herein in either the nature or location of the substituent moieties added. A thorough treatment of photoaffinity labelling compounds can be found in *Methods of Enzymology*, Vol. XLVI, (1977), Academic Press, N.Y., eds. W. B. Jakoby and Meir Wilchek. Some examples of these kinds of compounds are 8-azido derivatives of both cAMP and cGMP (B. E. Haley, Biochemistry, 14, 3852, (1975) and B. E. Haley, Methods in Enzymology, XLVI, 339–346, (1977)) and methylanthraniloyl addition to the 2'position of cGMP and cAMP (T. Hiratsuka, *J. Biol. Chem.*, 257, 11354–13358, (1982)). Two fluorescent analogs of cAMP, 1,N-etheno-cAMP (J. A. Secrist, III, J. R. Barrio, N. J. Leonard, C. Villar-Palasi and A. G. Gilman, *Science*, 177, 279–280, (1972)) and 1,N-etheno-aza-cAMP (K. C. Tsou, K. F. Yip and L. W. Lo, *Anal. Biochem.*, 60, 163–169, (1974)) have been reported, however, both analogs have altered adenine ring structures.

None of the above described heretofore reported compounds have been employed as therapeutic agents for the treatment of glaucoma or any other medical condition.

SUMMARY OF THE INVENTION

The present invention concerns a 2'-0-(4-benzoyl)-benzoyl nucleoside cyclic monophosphate of the formula (I)

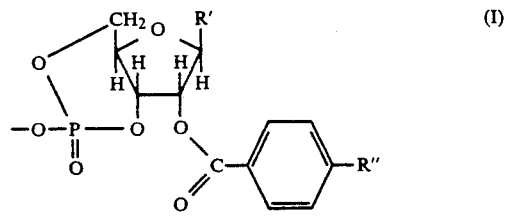

, wherein

R' is a purine base, a pyrimidine base, hydroxy, alkyl having 1 to 12 carbons atoms, cycloalkyl having 3 to 8 carbon atoms, alkoxy having 1 to 12 carbon atoms, aryl, halogenoalkyl having 1 to 12 carbon atoms, halogenoalkoxy having 1 to 12 carbon atoms, alkylthio having 1 to 12 carbon atoms, amino, nitro, azido, thiol, halogenoalkylthiol having 1 to 12 carbon atoms, a sugar containing bacbones with 3 to 6 carbon atoms, hydrogen, an alkene having 2 to 12 carbon atoms, an alkyne having 2 to 12 carbon atoms, an ether having up to 12 carbon atoms, an aldehyde having up to 12 carbon atoms, a ketone having up to 12 carbon atoms, a carboxylic acid having up to 12 carbon atoms, an ester having up to 12 carbon atoms or an amide having up to 12 carbon atoms and R" is hydrogen, halogen, alkyl having 1 to 12 carbon atoms, cycloalkyl having 3 to 8 carbon atoms, aryl, nitro, amino, cyano, thiol, alkoxy having 1 to 12 carbon atoms, alkylthio having 1 to 12 carbon atoms, halogenoalkyl having 1 to 12 carbon atoms, halogenoalkoxy having 1 to 12 carbon atoms, halogenoalkythio having 1 to 12 carbon atoms, azido, a sugar containing backbones with 3 to 6 carbon atoms, an alkene having 2 to 12 carbon atoms, an alkyne having 2 to 12 carbon atoms, an ether having up to 12 carbon atoms, an aldehyde having up to 12 carbon atoms, a ketone having up to 12 carbon atoms, a carboxylic acid having up to 12 carbon atoms, an ester having up to 12 carbon atoms or an amide having up to 12 carbon atoms, and physiologically acceptable salts thereof.

The present invention further concerns a method of lowering intraocular pressure in a warm blooded animal by administering to an eye of the warm blooded animal an effective intraocular pressure lowering amount of a 2'-O(4-benzoyl)benzoyl nucleoside cyclic monophosphate as described above, either alone or in admixture with a diluent.

The present invention is also directed to amethod of photoaffinity labelling a protein which binds cyclic AMP or cyclic GMP comprising contacting a protein which binds cyclic AMP or cyclic GMP with a 2'-0-(4-benzoyl)benzoyl nucleoside cyclic monophosphate as described above.

Still further, the present invention relates to a method of treating a warm blooded animal suffering from a physiological condition wherein a cyclic nucleotide is involved comprising administering to said warm blooded animal an effective amount of a 2'-0-(4-benzoyl)benzoyl nucleoside cyclic monophosphate as described above, either alone or in admixture with a diluent.

DETAILED DESCRIPTION OF THE INVENTION

Figure 1:
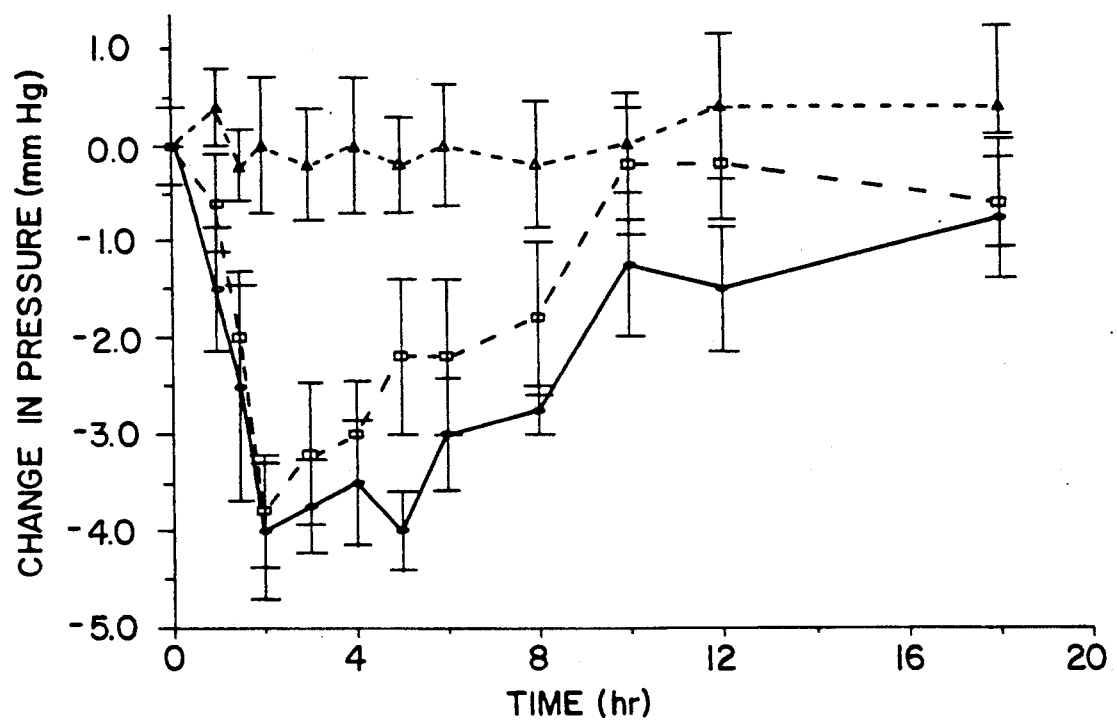
FIG. 1 is a graph of change in intraocular pressure of normal rabbits versus time for increasing concentrations of a compound according to the present invention, namely, 2'-0-(4-benzoyl)benzoyl guanosine 3',5'cyclic monophosphate.

In formula (I) alkyl represents a straight-chain or a branched hydrocarbon radical having 1 to 12 carbon atoms. Lower alkyl having 1 to about 6 carbon atoms is preferred. Non-limiting examples of alkyl are methyl, ethyl, propyl, isopropyl, butyl, isobutyl, pentyl, isopentyl, hexyl, isohexyl, heptyl, isoheptyl, octyl and isooctyl. The alkyl can be substituted, for example, by sulfur.

In formula (I), cycloalkyl represents a cyclic hydrocarbon radical having 3 to 8 carbon atoms. Non-limiting examples of cycloalkyl are cyclopentyl, cyclohexyl, cycloheptyl and cyclooctyl. The term cycloalkyl also includes cycloalkyl alkyl, e.g., cyclopropylmethyl through cyclopropylbutyl or cyclohexylmethyl.

In formula (I) alkoxy represents a straight-chain or branched hydrocarbon radical which has 1 to 12 carbon atoms and is bonded via an oxygen atom. Lower alkoxy having 1 to 6 carbon atoms is preferred. An alkoxy radical having 1 to 4 carbon atoms is particularly preferred. Non-limiting examples of alkoxy are methoxy, ethoxy, propoxy, isopropoxy, butoxy, isobutoxy, pentoxy, isopentoxy, hexoxy, isohexoxy, heptoxy, isoheptoxy, octoxy or isooctoxy.

In formula (I) aryl represents an aromatic ardical having one to three aromatic rings. Aryl can be substituted, for example, by a halogen, e.g., chlorine, fluorine, bromine or iodine, a $c_1$–$C_{12}$-alkyl, hydroxy, a $C_2$–$C_{12}$ alkene, amino, nitro or sulfur. Preferred aryl radicals are phenyl, naphthyl, anthracyl, phenoanthryl and biphenyl. Also aryl includes substituted aryl such as phenoxy, tolyl, clorophenyl, bromophenyl, fluorophenyl, nitrophenyl and phenylthio.

In formula (I), halogen represent fluorine, chlorine, bromine or iodine, preferably fluorine, chlorine or bromine.

In formula (I), the halogen part of halogenoalkyl and halogenoalkylthio comprises fluorine, chlorine, bromine or iodine and the alkyl part is a straight-chain or branched hydrocarbon having 1 to 12, and preferably 1 to 6, carbon atoms.

In formula (I), halogenoalkoxy comprises a halogen such as fluorine, chlorine, bromine or iodine and a straight-chain or branched alkoxy having 1 to 12, and preferably, 1 to 6 carbon atoms.

In formula (I), the purine or pyrimidine base is selected from the group consisting of azopyrimidine, xanthine, substituted xanthine, for example, hypoxanthine, guanine, substituted guanine, for example, 8-bromoguanine, 8-chloroguanine, 8-aminoguanine, 8-hydrazinoguanine, 8-hydroxyguanine, 8-methylguanine, 8-thioguanine and 3-deazaguanine, purine, substituted purine, for example, 2-aminopurine, 2,6-diaminopurine and azopurine, cytosine, substituted cytosine, for example, 5-ethylcytosine and 5-methylcytosine, thymine, substituted thymine, uracil, 5-substituted uracil, for example, 5-chlorouracil, 5-bromouracil, 5-ethyluracil, 5-iodouracil, 5-propyluracil and 5-vinyluracil, adenine and substituted adenine, for example, 3-deazaadenine.

In formula (I), non-limiting examples for alkenes are ethylene, allene, propylene, isobutylene and isoprene.

In formula (I), non-limiting examples of alkynes are acetylene and methylacetylene.

In formula (I), non-limiting examples of ethers are dimethyl ether, diethyl ether, diisopropyl ether and methyethylether.

In formula (I), non-limiting example of amides are acetamide, acetanilide, benzanilide, hexanamide and sulfanilamide.

In formula (I), non-limiting examples of ketones are acetone, emthylethylketone, acetophenone and benzophenone.

In formula (I), non-limiting examples of aldehydes are formaldehyde, acetaldehyde, propionaldehyde, butyraldehyde and beanzaldehyde.

In formula (I), non-limiting examples of carboxylic acids are ethanolic acid (acetic acid), propanoic acid (propionic acid), 2 methylpropanoic acid (isobutyric acid), benzoic acid, formic acid, valeric acid and caproic acid.

In formula (I), non-limiting examples of esters are methyl acetate, ethyl acetate, propyl acetate, ethyl butyrate, isoamyl acetate, isobutyl propionate and methyl salicylate.

In formula (I), non-limiting examples of sugars are glucose, fructose, galactose, ribose, deoxy-ribose, allose, gulose, mannose and glucopyranose.

In formula (I), a preferred moiety for R' is

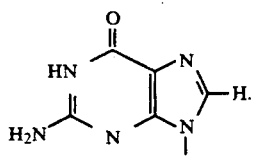

A preferred compound according to the present invention is 2'-0-(4-benzoyl)benzoylguanosine 3',5'cyclic monophosphate of the formula

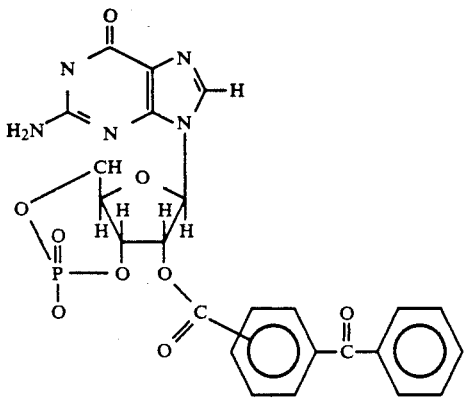

The compounds of the present invention can exist as optical isomers and both racemic and diastereomeric mixtures of these isomers which may exist for certain compounds, as well as the individual optical isomers are all within the scope of the present invention. While the racemic mixtures can be separated into their individual isomers through well-known techniques such as, for example, the separation of diastereomeric salts formed with optically active adjuncts, e.g., acids or bases followed by conversion back to the optically active substrates; in most instances, for the compounds of the present invention, the preferred optical isomer can be synthesized by means of sterospecific reactions, beginning with the appropriate stereoisomer of the desired starting material.

The present invention also pretains to pharmaceutically acceptable non-toxic salts of these compounds, containing, for example $Na^+$, $Li^+$, $K^+$, $Ca^{++}$ and $Mg^{++}$. Such salts may include those derived by combination of appropriate cations such as alkali and alkaline earth metal ions or ammonium and quaternary amino ions. Metal salts can be prepared by reacting the metal hydroxide with a compound of this invention. Examples of metal salts which can be prepared in this way are salts containing $Li^+$, $Na^+$, and $K^+$. A less soluble metal salt can be precipitated from the solution of a more soluble salt by addition of the suitable metal compound. In addition, salts may be formed from acid addition of certain organic and inorganic acids, e.g., HCl, HBr, $H_2SO_4$ or organic sulfonic acids. Finally, it is to be understood that compounds of the present invention in their un-ionized, as well as zwitterionic form, and/or in the form, of solvates are also considered part of the present invention.

The present invention includes pharmaceutical compositions containing as an active ingredient 2'-0-(4-benzoyl)benzoyl nucleoside cyclic monophosphate in admixture with a solid, liquid or liquefied gaseous diluent.

The invention further provides a pharmaceutical composition containing as an active ingredient the 2'-0-(4-benzoyl)benzoyl nucleoside cyclic monophosphate in the form of a sterile and/or physiologically isotonic aqueous solution.

The invention also provides a medicament in the form of tablets (including lozenges and granules), caplets, dragees, capsules, pills, ampoules or suppositories comprising 2'-0-(4-benzoyl)benzoyl nucleoside cyclic monophosphate.

"Medicament" as used herein means physically discrete coherent portions suitable for medical administration. "Medicament in dosage unit form" as used herein means physically discrete coherent units suitable for medical administration, each containing a daily dose or a multiple (up to four times) or a sub-multiple (down to a fortieth) of a daily dose of the compound of the invention in association with a carrier and/or enclosed within an envelope. Whether the medicament contains a daily dose, or, for example, a half, a third or a quarter of a daily dose will depend on whether the medicament is to be administered once or, for example, twice, three times or four times a day, respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g., granulates) adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethylene glycols.

The tablets, dragees, capsules, caplets and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substance or waxes.

The active ingredient can also be made up in microencapsulated form together, with one or several of the above-mentioned diluents.

The diluents to be used in pharmaceutical compositions adapted to be formed into suppositories can, for example, be the usual water-soluble diluents, such as polyethylene glycols and fats (e.g., cocoa oil and high esters, [e.g., $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200, except in the presence of a surface-active agent), such solvents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil), glycerol, tetrahydrofurfuryl alcohol, polyethylene glycols and fatty acid esters of sorbitol or mixtures thereof.

For parenteral administration, solutions and emulsions should be sterile and, if appropriate, blood-isotonic.

The pharmaceutical compositions which are suspensions can contain the usual diluents, such as liquid diluents, e.g., water, ethyl alcohol, propylene glycol, surface-active agents (e g., ethoxylated isostearyl alcohols, polyoxyethylene sorbite and sorbitane esters) microcrystalline cellulose, aluminum metahydroxide, bentonite, agar-agar and tragacanth or mixtures thereof.

The inventive compound favors organic solvents; the upper limit of solubility in water, ethanol or methanol and DSMO is approximately 100 mM. Butanol is also a good solvent, but probably not a very good vehicle.

In DMSO, the compound remains in solution and does not degrade when stored at −20° C. No preservative need be added.

pH most likely would alter solubility, especially in the aqueous solvents, i.e., lowering pH would no doubt lower solubility of the inventive compound. However, pH hovers between 6 and 7 in DMSO (tested by diluting into $H_2O$). Addition of 10–100 mM HEPES buffer, pH 7.2, to aqueous solutions of the compound is without effect.

Osmolality is approximately equal to molarity.

The solution is clear, colorless (except for the absorbance peak of the compound at 260 nm) and odorless.

All the pharmaceutical compositions according to the invention can also contain coloring agents and preservatives, as well as perfumes and flavoring additives (e.g., pepperminet oil and eucalyptus oil) and sweetening agents (e.g., saccharin and aspartame).

The pharmaceutical compostions according to the invention generally contain from 0.5 to 90% of the active ingredient 2'-0-(4-benzoyl)benzoyl nucleoside cyclic monophosphate) by weight of the total composition.

In addition to 2'-0-(4-benzoyl)benzoyl nucleoside cyclic monophosphate, the pharmaceutical compositions and medicaments according to the invention can also contain other pharmaceutically active compounds.

A diluent in the medicaments of the present invention may be any of those mentioned above in relation to the pharmaceutical compositions of the present invention. Such medicaments may include solvents of molecular weight less than 200 as the sole diluent.

The discrete coherent portions constituting the medicament according to the invention will generally be adapted by virtue of their shape or packaging for medical adminstration and may be, for example, any of the following: tablets (including lozenges and granulates), pills, dragees, capsules, suppositories and ampoules. Some of these forms may be made up for delayed release of the active ingredient. Some, such as capsules, may include a protective envelope which renders the portions of the medicament physically discrete and coherent.

The preferred daily dose for administration of the medicaments of the invention is 2.5 to 250 mg of active ingredient in the case of intravenous administration and 25 to 250 mg of active ingredient in the case of oral administration.

The process for producing the above-mentioned pharmaceutical compositions and medicaments is carried out by any method known in the art, for example, by mixing the active ingredient(s) with the diluent(s) to form a pharmaceutical composition (e.g., a granulate) and then forming the composition into the medicament (e.g., tablets).

This invention provides a method for reducing intraocular pressure in warm-blooded animals, e.g., humans, which comprises topically administering to an eye or eyes of a warm blooded animal the compound of the invention, namely, 2'-0-(4-benzoyl)benzoyl nucleoside cyclic monophosphate, alone or in admixture with a diluent.

The inventive compounds are also useful to treat physiological conditions wherein cyclic nucleotides are involved, for example, to treat warm blooded animals, e.g., humans, suffering from glaucoma, heart disease, viral diseases, stroke, arterosclerosis, cancer, depression, allergies, asthma, analgesia, Parkinson's disease, dermatitis, e.g., psoriasis, and learning and memory disorders.

For treating eye diseases and some skin conditions, it is preferred that the inventive compound be topically administered. For treating other physiological conditions and for treating certain skin conditions, it is preferred that the inventive compound be systemically administered.

The active compound of this invention,is also useful as a drug in certain neurological or psychological pathologies. To treat such pathologies in warm blooded animals, e.g., humans, or to treat other physiological conditions where systemic administration is preferred the active compound, alone or in admixture with a diluent can be administered perorally, parenterally (for example, intramuscularly, intraperitoneally, subcutaneously or intravenously), rectally or locally, preferably orally or parenterally, especially perlingually or intravenously. Preferred pharmaceutical compositions and medicaments to treat neurological or psychological pathologies and to treat other physiological conditions where systemic adminsitration is preferred are, therefore, those adapted for administration such as oral or parenteral administration.

To treat neurological or psychological pathologies and to treat other physiological conditions where systemic adminsitration is preferred it is advantageous to administer intravenously amounts of from 0.01 to 10 mg/kg, preferably 0.05 to 5 mg/kg, of body weight per day and to administer orally 0.05 to 20 mg/kg, preferably 0.5 to 5 mg/kg of body weight per day, to achieve effective results. Nevertheless, it can at times be necessary to deviate from those dosage rates, and in particular to do so as a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than the above-mentioned minimum dosage rate, whilst other cases the upper limit mentioned must be exceeded to achieve the desired results. Where larger amounts are administered, it may be advisable to divide these into several individual administrations over the course of the day.

The 2'-0-(4-benzoyl)benzoyl nucleoside cyclic monophosphate of the invention is a potent inhibitor of the cyclic GMP phosphodiesterase found in phosphodiesterases from other tissues.

The inventive 2'-0-(4-benzoyl)benzoyl nucleoside cyclic monophosphate is also valuable as a photoaffinity label for proteins which bind cyclic GMP.

The inventive compound is photoreactive, that is, illumination with near UV light causes formation of a diradical triplet state of the benzophenone group allowing it to abstract a proton and form a covalent bond with nearby molecules such as proteins.

The invention will now be described with reference to the following non-limiting examples.

Example 1: Preparation of 2'-0-(4-benzoyl)benzoyl-guanosine 3',5' cyclic monophosphate (1) 10 g of carbonyldiimidazole are mixed with 5 g of benzoylbenzoic acid in dimethylformamide and the resultant mixture is left to stand for 15 minutes at room temperature.

(2) 5 g of 3',5'-cyclic guanosine monophosphate are dissolved in 200 ml of distilled water and brought to a pH of 7.0.

Solutions (1) and (2) are combined and allowed to react overnight (protected from light) at room temperature.

The solvents are evaporated off.

The product is resuspended in distilled water and purified from the reactants by conventional or high pressure chromatography. Successful techniques employed include a $C_{18}$ reverse phase column with methanol gradient elution or silica gel column with isocratic butanol elution.

Example 2: Preparation of 2'-0-(4-benzoyl)benzoyl-adenosine 3',5' cyclic monophosphate (1) 10 g of carbonyldiimidazole are mixed with 5 g of benzoylbenzoic acid in dimethylformamide and the resultant mixture is left to stand for 15 minutes at room temperature.

(2) 5 g of 3',5'-cyclic adenosine monophosphate are dissolved in 200 ml of distilled water and brought to a pH of 7.0.

Solutions (1) and (2) are combined and allowed to react overnight (protected from light) at room temperature.

The solvents are evaporated off.

The product is resuspended in distilled water and purified from the reactants by conventional or high pressure chromatography. Successful techniques employed include a $C_{18}$ reverse phase column with methanol gradient elution or silica gel column with isocratic butanol elution.

Example 3: Testing of the Effects of the Inventive Compound in Lowering Intraocular Pressure in Animals Non-pigmented, normal (non-water-loaded) rabbits received topical administration to their eyes of 2'-0-(4)-benzoyl benzoyl guanosine 3',5'cyclic monophosphate as prepared according to Example 1.

Figure 2:
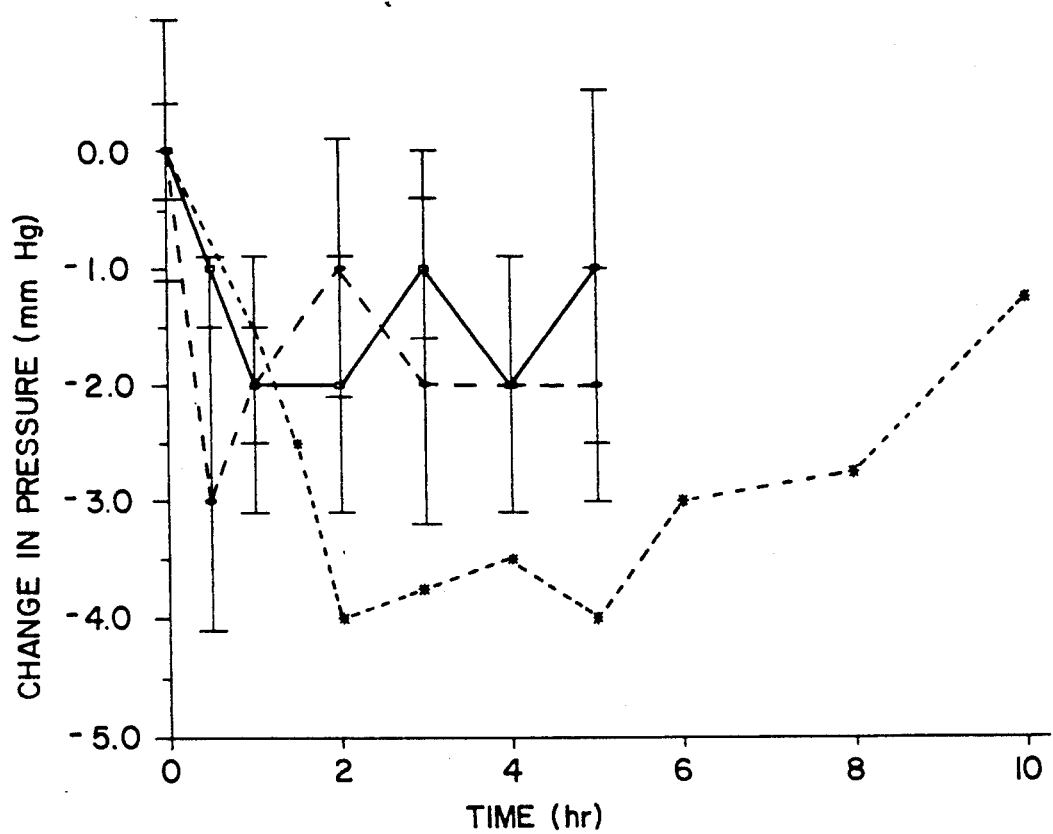
FIG. 2 is a graph of change in intraocular pressure of normal rabbits versus time for timolol vs. a compound according to the present invention, namely, 2'-0-(4-benzoyl)benzoyl guanosine 3',5'cyclic monophosphate.

The mean baseline IOP (intraocular pressure) for the rabbits was 17.5 mm Hg. It should be noted that the data presented in FIG. 1 and FIG. 2 are relative to time zero and normalized relative to the contralateral eye. The contralateral eye received a DMSO control lacking the inhibitor compound. It is believed that this is the most conservative way to represent the data.

Figure 3:
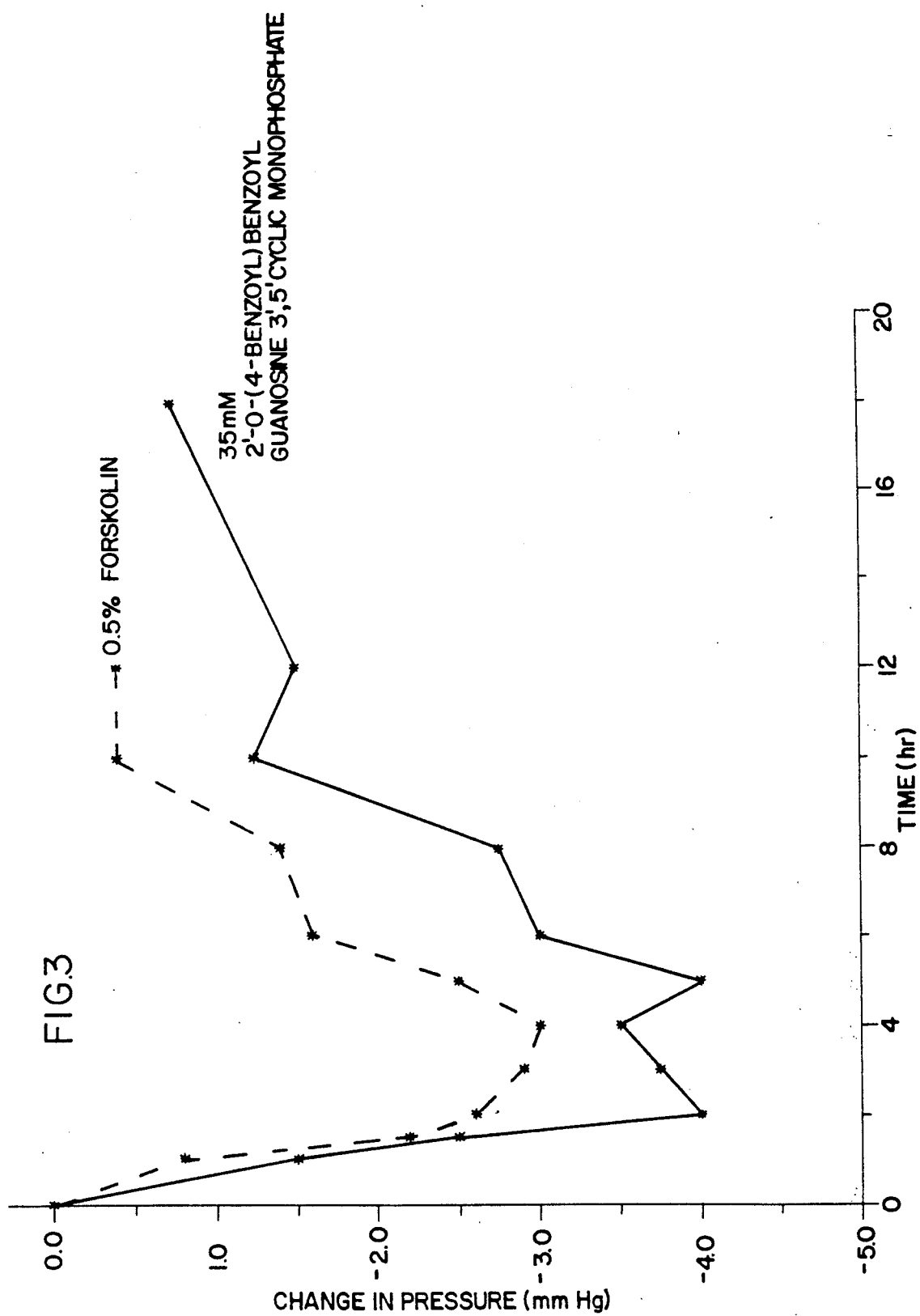
FIG. 3 is a graph of change in intraocular pressure of normal rabbits versus time for Forskolin vs. a compound according to the present invention, namely, 2'-0-(4-benzoyl)benzoyl guanosine 3',5'cyclic monophosphate.

Ten of the rabbits were given the forskolin test (see FIG. 3).

Additionally, five rabbits were administered 2'-0-(4-benzoyl)benzoyl guanosine 3',5'cyclic monophosphate (and DMSO) in a sterile saline solution diluted 10- and 100-fold.

FIG. 1 depicts the results of increasing concentrations of 2'-0-(4-benzoyl)benzoyl guanosine 3',5' cyclic monophosphate on the intraocular pressure of normal rabbits. Pressures ($\pm$S.E.M) are relative to pressure at time zero and normalized with respect to that of the contralateral eye. Contralateral eyes received solutions containing (DMSO) vehicle without 2'-0-(4-benzoyl)benzoyl guanosine 3',5'cyclic monophosphate. Open circles in FIG. represent 50 $\mu$l of 35 mM 2'-0-(4-benzoyl)benzoyl guanosine 3',5'cyclic monophosphate in DMSO administered at time (t)=0. Open squares in FIG. 1 depict 50 $\mu$l of saline solution containing 10% DMSO (v/v) and 3.5 mM 2'-0-(4-benzoyl)benzoyl guanosine 3',5'cyclic monophosphate. Open triangles in FIG. 1 depict 50 $\mu$l of saline containing 1% DMSO and 350 $\mu$M 2'-0-(4-benzoyl)benzoyl guanosine 3',5' cyclic monophosphate. Intraocular pressure was measured by applanation tonometry (using an Alcon Applanation Pneumotonograph) after topical application of proparacaine HCl 0.05%. No significant change in pupil diameter was observed in either eye at any concentration of the compound, i.e., the 10-fold diluted material (approximately 3 mM) had about the same effect on IOP, while the 100-fold diluted compound (approximately 0.3 mM) appeared to have essentially no effect.

FIG. 2 depicts the effects of Timolol vs. 2'-0-(4-benzoyl)benzoyl benzoyl guanosine 3',5'cyclic monophosphate on intraocular pressure of normal rabbits. Data for Timolol was based on Vareilles, P., Silverstone, D., Plazonnet, B., Le Douarec, J. C., Sears, M. L., & Stone, C. A., *Invest. Ophthalmol. and Visual Science*, 16: 987 (1977).

Pressures ($\pm$S.E.M.) were relative to pressure at time zero and normalized with respect to that of the contralateral eye. N=14 for each of the Timolol experiments. Open squares represent 100 $\mu$l of saline containing 0.01% (w/v) Timolol were applied topically at t=0. Open circles represent 100 $\mu$l of saline containing 0.1% Timolol applied topically. The data points without error bars (35 mM 2'-0-(4-benzoyl)benzoyl guanosine 3',5'cyclic monophosphate) are mean values reproduced from FIG. 1 for comparison.

In using the inventive compound, no lid erythema or ciliary injection were observed. At full concentration (in straight DMSO) slight conjunctival hyperemia was noticed; this was reduced when the compound (and DMSO) was diluted ten-fold with saline solution.

FIG. 3 depicts the effects of 2'-0-(4-benzoyl)benzoyl guanosine 3',5'cyclic monophosphate vs. forskolin on intraocular pressure of normotensive rabbits. Intraocular pressure was relative to pressure at time zero and normalized with respect to the contralateral eye. At time zero, 50 $\mu$l of 2'-0-(4-benzoyl)benzoyl guanosine 3',5'cyclic monophosphate, suspended in DMSO, was applied to the right eye of four rabbits. Intraocular pressure was measured by applanation tonometry after topical application of 0.05% proparacaine. The forskolin data were the results of application of 0.5% forskolin in buffered saline to the eyes of ten normotensive rabbits.

Figure 4:
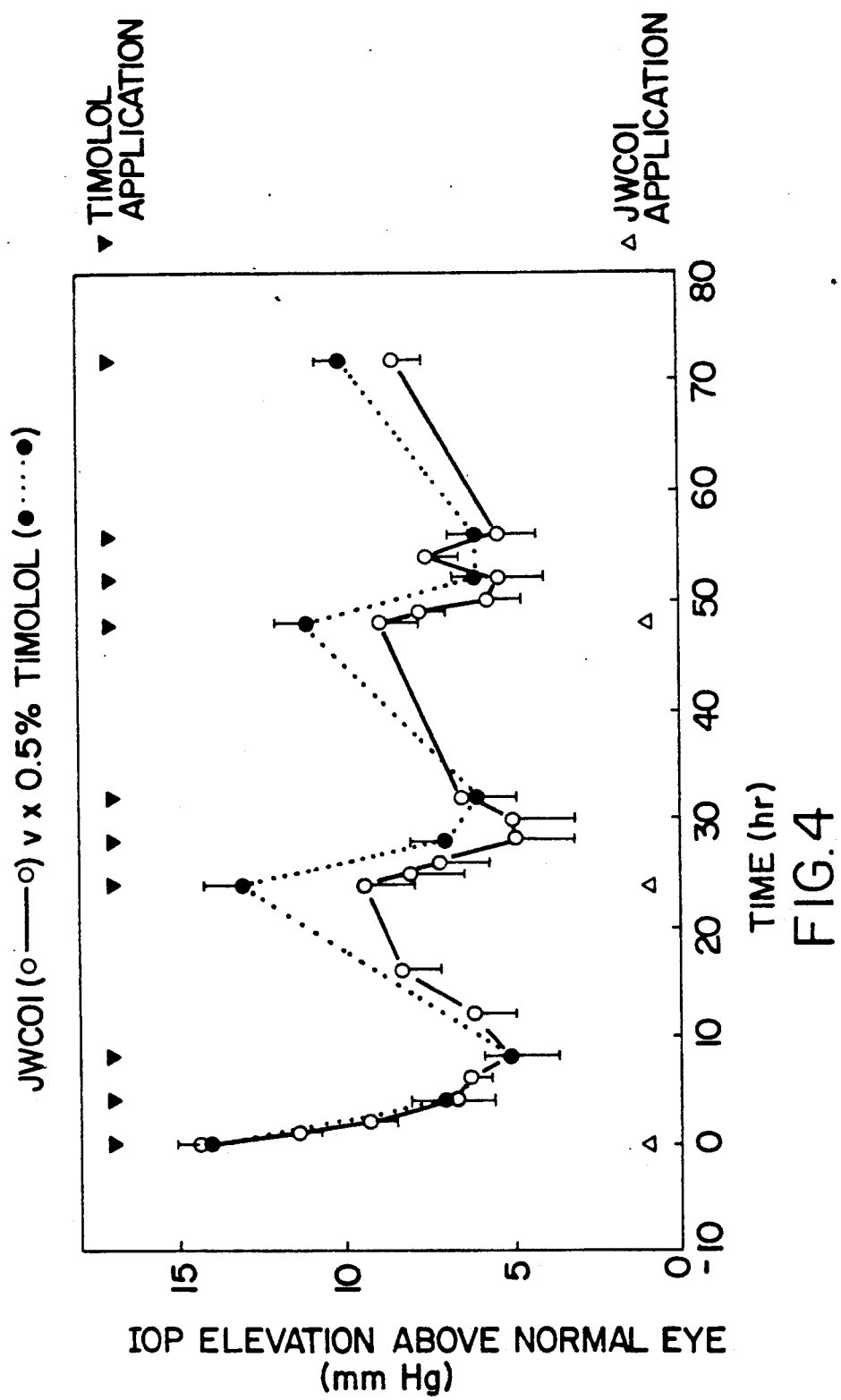
FIG. 4 is a graph depicting the effect of repeated doses of 2'-0-(4-benzoyl)benzoyl guanosine 3',5'cyclic monophosphate vis. Timolol on hypertensive rabbit eyes.
Figure 5:
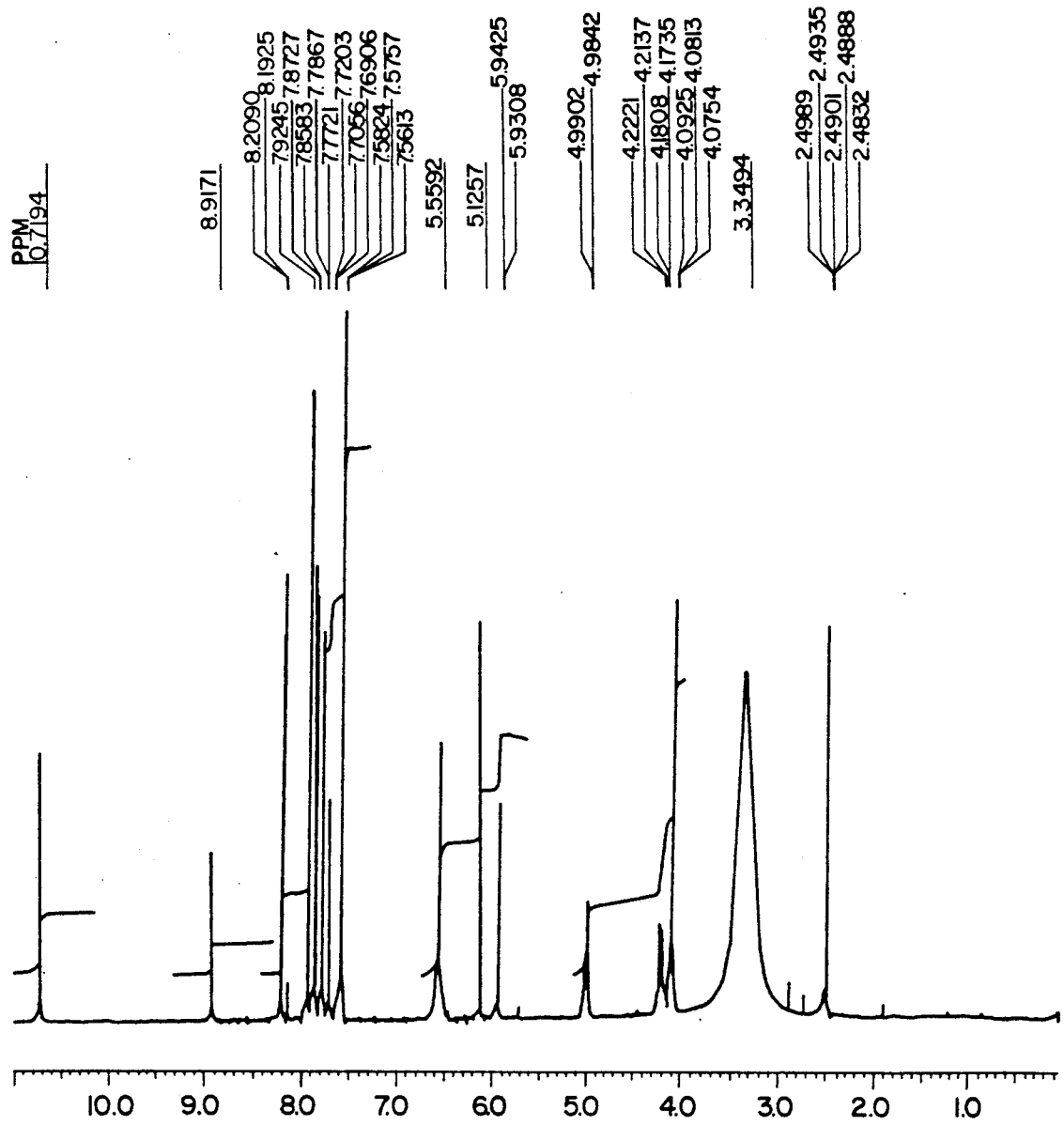
FIG. 5 is a proton NMR spectrum of 5 mM of 2'-0-(4-benzoyl)benzoyl guanosine 3',5'cyclic monophosphate in $D^2$DMSO, pH 7.0 (the "$D^2$" in DMSO is deuterium).
Figure 6:
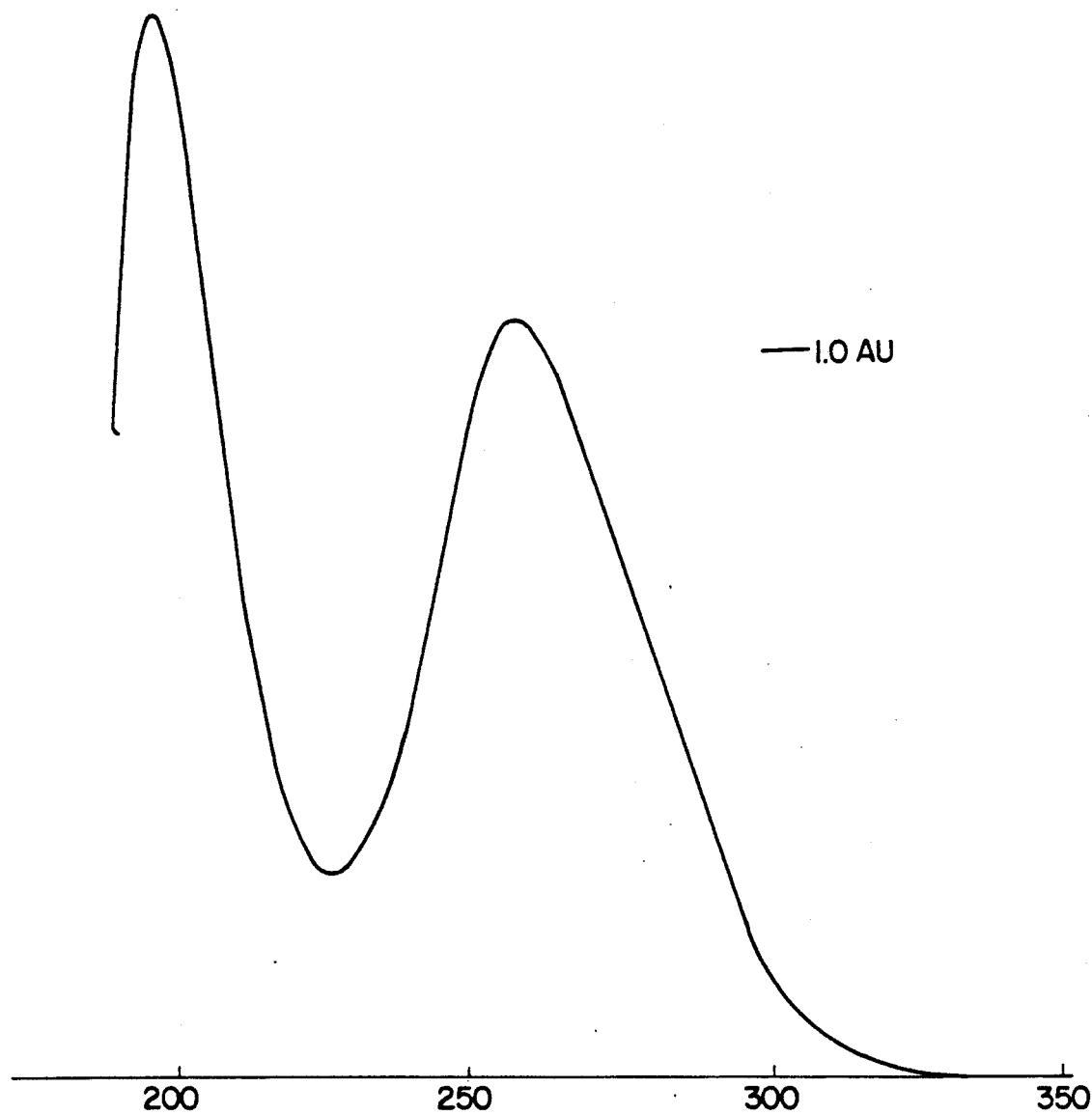
FIG. 6 depicts the UV-visible absorbance spectrum of the sodium salt of 2'-0-(4-benzoyl)benzoyl guanosine 3',5'cyclic monophosphate in water, concentration of 27 $\mu$M, pH=7.0. The absorbance spectrum was measured in a Shimadzu UV-3000 dual wavelength, dual beam.

FIG. 4 depicts the effect of repeated doses of 2'-0-(4-benzoyl)benzoyl guanosine 3',5'cyclic monophosphate vs. Timolol on hypertensive Rabbit Eyes. Rabbits with chymotrypsin-induced, ocular hypertension were treated on 3 successive days (as indicated by the open 2'-0-(4-benzoyl)benzoyl guanosine 3',5'cyclic monophosphate Intraocular pressure was measured by applanation tonometry (as described above). The open circles show the intraocular pressure elevation in the hypertensive eyes relative to the control eyes from rabbits treated with 2'-0-(4-benzoyl)benzoyl guanosine 3',5'cyclic monophosphate. The closed circles show intraocular pressure in hypertensive eyes treated with repetitive doses of 0.5% Timolol (from Vareilles et al, 1977, supra). The closed triangles show the times of Timolol instillation.

Example 4: The Inventive Compound as an Inhibitor of the cGMP and cAMP Phosphodiesterases 2'-0-(4-benzoyl)benzoyl guanosine 3',5' cyclic monophosphate was assayed as an inhibitor of the cGMP and cAMP phoosphodiesterases in rat bladder. The inhibition of the two PDEases were assayed as per J. N. Wells, C. E. Baird, Y. J. Wu and J. G. Hardman, *Biochem. Biophys. Acta*, 384, 430, (1975). Expressed as IC$_{50}$'s, the concentration required to cause 50% inhibition of the enzynme were as follows:

cGMP PDE: 0.5 μM
cAMP PDE: 15.8 μM

Table 1 hereinbelow lists inhibitors of rod light-activated PDEase.

TABLE 1

| Inhibitors of Rod Light-Activated PDEase | |
|---|---|
| Inhibitor | K$_i$ for Inhibition, μM |
| Prior Art Materials | |
| cGMP | 40.0 (Km)[a] |
| (R$_p$)-cGMP [S] | 90.0[a] |
| (S$_p$)-cGMP [S] | 25.0[a] |
| 8-Br-cGMP | 48.0[a] |
| N$^2$,O$^2$,-dibutyryl-cGMP | 66.0[a] |
| N$^2$-monobutyryl-cGMP | 258.0[a] |
| O$^2$,-monobutyryl-cGMP | 18.0[a] |
| 2'-Deoxy-cGMP | 76.0[a] |
| Isobutylmethylxanthine | ~100.0[b] |
| Theophyline | ~360.0[b] |
| Papaverine | ~50.0[b] |
| Inventive Compound | 0.3 |
| 2'-0-(4-benzoyl) benzoyl quanosine 3',5' cyclic monophosphate | |

[a]A. L. Zimmerman et al, (1985), Proc. Natl. Acad. Sci. USA, 82, 8813–8817.
[b]Interpolated from R. G. Pannbacker et al, (1972), Science, 175, 757–756, and G. Chader et al, (1974), Exp. Eye Res., 18, 509–515.

Figure 7:
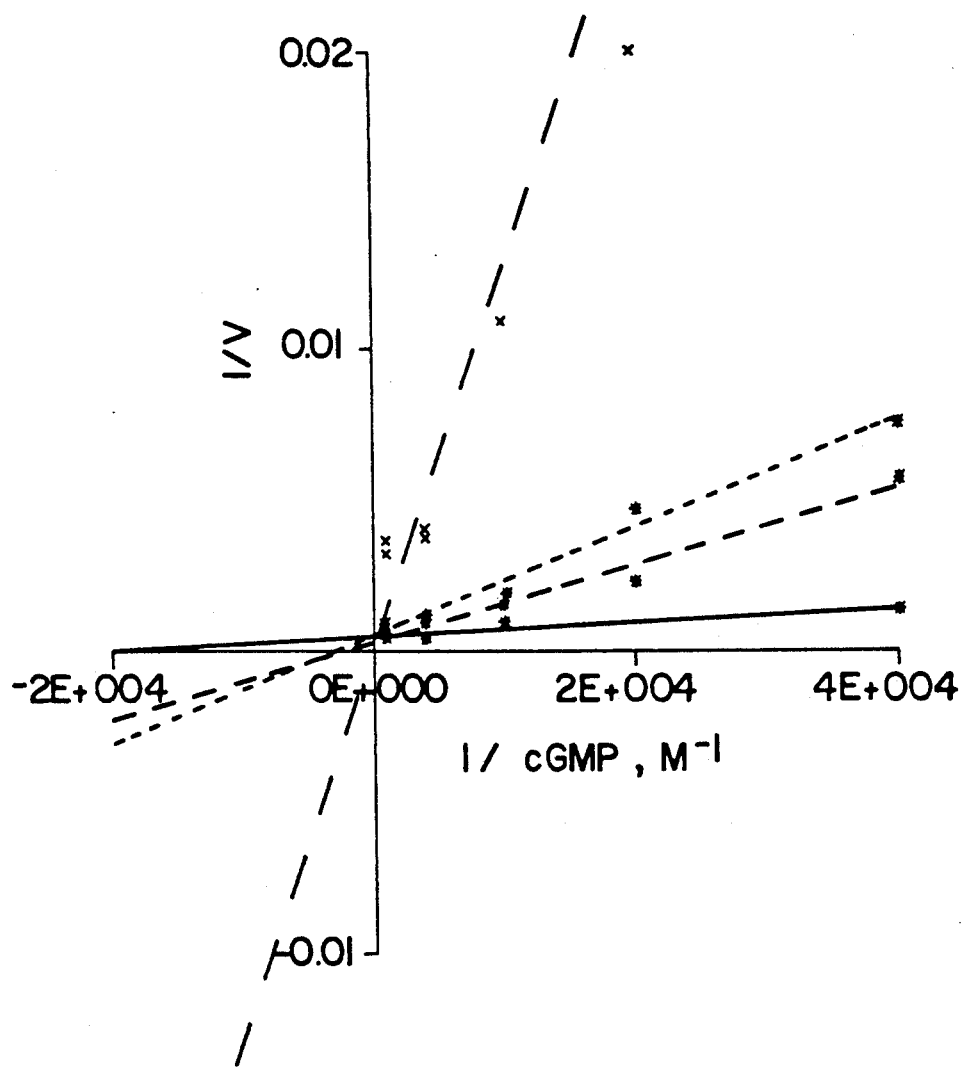
FIG. 7 shows a Lineweaver-Burke analysis of the inhibitory effectiveness of 2'-0-(4-benzoyl)benzoyl guanosine 3',5'cyclic monophosphate versus 8-Br-3',5' cyclic guanosine monophosphate.

Example 5: Lineweaver-Burke Analysis of Inhibitory Effectiveness of 2'-0-(4-benzoyl)benzoyl guanosine 3',5'cyclic monophosphate versus 8-Br-cGMP FIG. 7 depicts a Lineweaver-Burke analysis of inhibitory effectiveness of 2'-0-(4-benzoyl)benzoyl guanosine 3',5'cyclic monophosphate versus 8-Br-cGMP. The data illustrated are cGMP hydrolysis velocities from toad photoreceptor rod outer segment membranes containing 20 nM Type III cGMP phosphodiesterase in the presence of 100 mM NaCl, 1 mM Tris-HCl, 1 MgCl$_2$,20 μM p[NH]ppG (guanylylimididiphosphate), pH 7.4, and the indicated concentrations of substrate. Open squares indicate control velocities. Open diamonds are velocities in the presence of 25 μM 8-Br-cGMP (K$_i$ calculated from slope/K$_m$ ratios to be 6 μM). Open circles and open triangles show the effect of 2 μM and 20uM 2'-0-(4-benzoyl)benzoyl guanosine 3',5'cyclic monophosphate respectively (K$_i$=0.3 μM).

Example 6: Inhibition of Platelet Phosphodiesterase Activity

Figure 8:
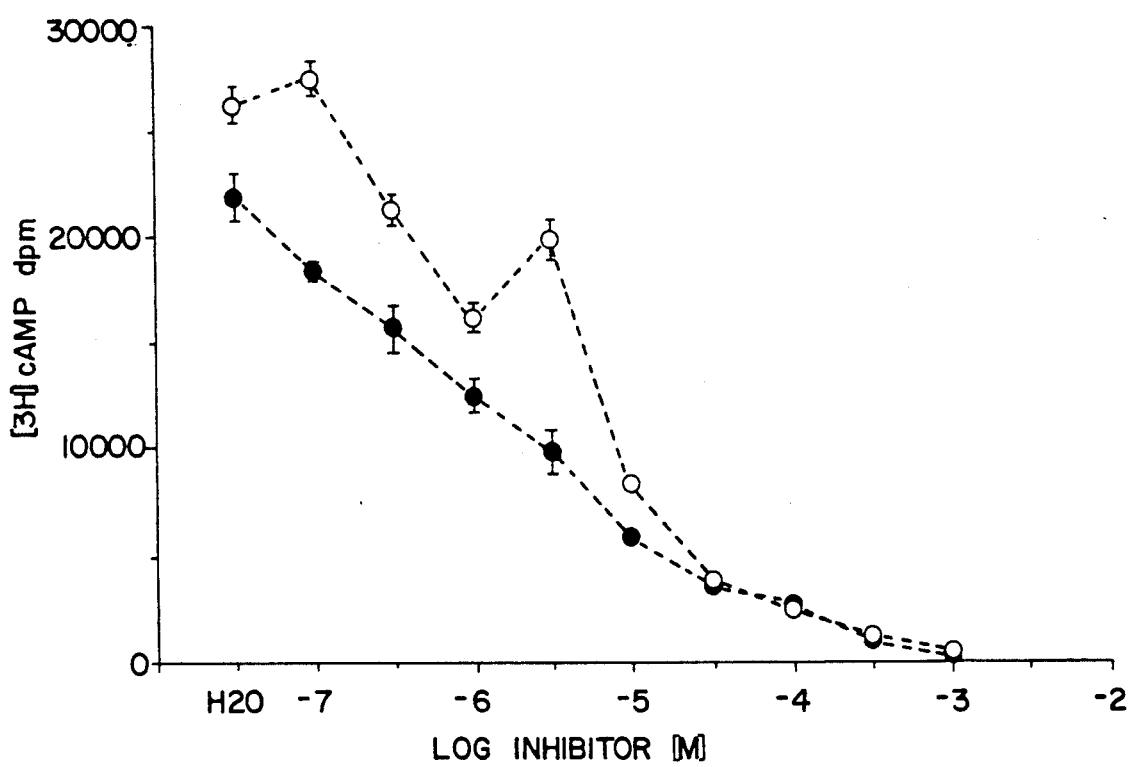
FIG. 8 is a graph depicting the inhibition of platelet phosphodiesterase activity of 2'-0-(4-benzoyl) benzoyl guanosine 3',5'cyclic monophosphate (closed circles) and 2'-0-(4-benzoyl)benzoyl cyclic adenosine monophsophate (open circles).

FIG. 8 shows the extent of inhibition of H$^3$-cAMP hydrolysis resulting incubation of platelet preparations with different concentrations of 2'-0-(4-benzoyl)benzoyl guanosine 3',5'cyclic monophosphate or 2'-0-(4-benzoyl) benzoyl cyclic adenosine monophosphate. Both compounds inhibited phosphodiesterase activity significantly. The IC$_{50}$'s for 2'-0-(4-benzoyl)benzoyl guanosine 3',5'cyclic monophosphate and 2'-0-(4-benzoyl)benzoyl cyclic adenosine monophosphate were 3 and 10 μM, repsectively. Enzyme activity was assayed by incubation of platelet preparations with H$^3$-cAMP for 5 minutes at 30° C. Activity was quenched by boiling the assay tubes for 1 minute. Each sample was run in triplicate. Analysis of H$^3$-cAMP was performed according to the procedure of W. J. Thompson, W. L. Terasaki, P. M. Epstein and S. J. Strada, "Assay of Cyclic Nucleotide Phosphodiesterase and Resolution of Multiple Molecular Forms of the Enzyme", *Adv. in Cyclic Nucleotide Research*, 10, 69–92 (1979).

It will be appreciated that the instant specification and examples are set forth by way of illustration and not limitation and that various modifications and changes may be made without departing from the spirit and scope of the present invention.

What is claimed is:

1. A 2'-0-(4-benzoyl)benzoyl nucleoside 3',5'-cyclic monophsophate of the formula (I)

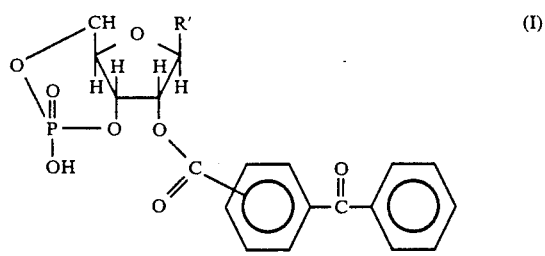

wherein, R' is guanine or adenine.

2. The compound according to claim 1 wherein R' is guanine.

3. The compound according to claim 1 wherein R' is adenine.

4. A topical ophthalmic pharmaceutical composition of the compound of claim 2 with a pharmaceutically acceptable diluent.

5. A topical ophthalmic pharmaceutical composition of the compound of claim 3 with a pharmaceutically acceptable diluent.

6. A method of reducing intraocular pressure in a warm-blooded animal comprising administering to an eye of a warm-blooded animal an effective intraocular pressure reducing amount of a 2'-0-(4-benzoyl)benzoyl nucleoside cyclic monophosphate according to claim 1.

7. The method according to claim 6 wherein R' is guanine.

8. The method according to claim 7 wherein R' is adenine.

* * * * *

UNITED STATES PATENT AND TRADEMARK OFFICE
CERTIFICATE OF CORRECTION

PATENT NO. : 5,039,797

DATED : August 13, 1991

INVENTOR(S) : Clack et al.

It is certified that error appears in the above-identified patent and that said Letters Patent is hereby corrected as shown below:

Col. 12, line 33   Delete " monophsophate " and substitute -- monophosphate --

Signed and Sealed this

Eighteenth Day of May, 1993

Attest:

MICHAEL K. KIRK

Attesting Officer

Acting Commissioner of Patents and Trademarks